(12) United States Patent
Zhang

(10) Patent No.: US 8,680,329 B2
(45) Date of Patent: Mar. 25, 2014

(54) PROCESS FOR PREPARATION OF α-KETOGLUTARIC ACID

(75) Inventor: Guoji Zhang, Tianjin (CN)

(73) Assignee: Tianjin Tiancheng Pharmaceutical Co., Ltd. (China), Tianjin (CN)

( * ) Notice: Subject to any disclaimer, the term of this patent is extended or adjusted under 35 U.S.C. 154(b) by 747 days.

(21) Appl. No.: 12/925,133

(22) Filed: Oct. 13, 2010

(65) Prior Publication Data

US 2012/0095261 A1    Apr. 19, 2012

(51) Int. Cl.
*C07C 229/26*    (2006.01)

(52) U.S. Cl.
USPC ........................................ 562/560

(58) Field of Classification Search
CPC ............................ C07C 279/14; C07C 59/237
See application file for complete search history.

(56) References Cited

U.S. PATENT DOCUMENTS 3,723,248 A * 3/1973 Tanaka et al. ................. 435/143
4,296,127 A * 10/1981 Walser .......................... 514/564

FOREIGN PATENT DOCUMENTS

| ES | 392277 A1 | * | 1/1974 |
| FR | CAM70 | * | 4/1965 |
| GB | 1199547 | * | 7/1970 |

* cited by examiner

*Primary Examiner* — Paul A Zucker
(74) *Attorney, Agent, or Firm* — Raymond Y. Chan; David and Raymond Patent Firm

(57) ABSTRACT

A process of preparation of α-ketoglutaric acid for mass production of L-arginine α-ketoglutarate 1:1 and 2:1 includes the steps of: reacting methyl dichloroacetate and acrylic acid methyl ester with sodium methoxide to obtain Dimethyl 2,2-dichloroglutarate; reacting the dimethyl 2,2-dichloroglutarate with hydroxide solution to obtain crude α-ketoglutaric acid aqueous solution; purifying the crude α-ketoglutaric acid aqueous solution to obtain purified α-ketoglutaric acid aqueous solution; and adjusting the concentration of the purified α-ketoglutaric acid aqueous solution by adding water. While avoiding the use of massive organic solvents, the process of the present invention has a remarkable high yield to realize mass production with low manufacturing cost and shortened production time.

2 Claims, 3 Drawing Sheets

8,680,329 B2

PROCESS FOR PREPARATION OF α-KETOGLUTARIC ACID

FIELD OF INVENTION

The present invention relates to a process of preparation of α-ketoglutaric acid, and more particularly to a process of preparation of α-ketoglutaric acid which avoids the massive use of organic solvent during preparation while achieving a high yield such that mass production of a high yield and low cost end product is realized.

DESCRIPTION OF RELATED ARTS

Alpha-ketoglutaric acid is an important biological molecular, which is a key intermediate in Krebs cycle, a nitrogen transporter, and a co-substance in molecular oxidation. It is used as a dietary supplement for body building and to enhance athletic performance. In addition, α-ketoglutaric acid is used for preparation of L-arginine α-ketoglutarate 1:1 & 2:1, which are widely used as sports nutrition ingredients.

However, conventional method of preparation of α-ketoglutaric acid, and L-arginine α-ketoglutarate 1:1 and 2:1 are complicated, time consuming and costly which are not suitable for industrialization. In particular, the conventional method makes use of large amount of organic solvents for the reactions which involves high production cost and lengthened production time is not suitable for mass production to meet the needs in the market.

SUMMARY OF THE PRESENT INVENTION

The invention is advantageous in that it provides a process of preparation of α-ketoglutaric acid which is cost effective and suitable for mass production.

Another advantage of the invention is to provide a process of preparation of α-ketoglutaric acid which does not require the use of a large amount of organic solvents throughout the process.

Another advantage of the invention is to provide a process of preparation of α-ketoglutaric acid through which a shorten period of production time is required to obtain a higher yield of final products.

Additional advantages and features of the invention will become apparent from the description which follows, and may be realized by means of the instrumentalities and combinations particular point out in the appended claims.

According to the present invention, the foregoing and other objects and advantages are attained by a process of preparation of α-ketoglutaric acid comprising the steps of:

(a.1) adding methyl dichloroacetate and acrylic acid methyl ester;

(a.2) starting stirring and setting a first controlled temperature of 0-60° C. through the reactor;

(a.3) adding sodium methoxide slowly to form a first reaction mixture;

(a.4) allowing reaction for 1 to 4 hours in the reactor at the first controlled temperature with stirring;

(a.5) washing the first reaction mixture with water twice, wherein 100 to 300 liter of water is used for each of the washing;

(a.6) separating and removing organic phase of the first reaction mixture in the step (a.5) and setting the reactor for distillation under reduced pressure to obtain dimethyl 2,2-dichloroglutarate, (b.1) mixing the dimethyl 2,2-dichloroglutarate obtained from step (a) with hydroxide solution at a second controlled temperature for 0.5 to 8 hours to form a second mixture;

(b.2) adding inorganic salt to the second mixture and stirring for 0.5 to 5 hours for precipitation of α-ketoglutarate salt;

(b.3) filtering the α-ketoglutarate salt out, adding water and inorganic acid to the α-ketoglutarate salt while stirring and adjusting pH to pH≤4.5;

(b.4) removing the inorganic salt through filtration to obtain the crude α-ketoglutaratic acid aqueous solution;

(c.1) passing the crude α-ketoglutaratic acid aqueous solution through cation exchange resin, anion exchange resin, and cation exchange resin to remove impurities to obtain a purified α-ketoglutaratic acid aqueous solution; and (c.2) adjusting a concentration of the purified α-ketoglutaratic acid aqueous solution to 25-55% by weight, thereby a yield of the purified α-ketoglutaratic acid aqueous solution is approximately 75% and no organic solvent is used throughout the process.

In accordance with another aspect of the invention, the present invention provides a process of preparation of α-ketoglutaric acid for mass production of L-arginine α-ketoglutarate 1:1 and 2:1, comprising the steps of:

(a) reacting methyl dichloroacetate and acrylic acid methyl ester with sodium methoxide to obtain dimethyl 2,2-dichloroglutarate;

(b) reacting the dimethyl 2,2-dichloroglutarate from step (a) with hydroxide solution to obtain crude α-ketoglutaratic acid aqueous solution;

(c) purifying the crude α-ketoglutaratic acid aqueous solution to obtain purified α-ketoglutaratic acid aqueous solution; and (d) adjusting a concentration of the purified α-ketoglutaratic acid aqueous solution by adding water, (e.1") setting a concentration of the purified α-ketoglutaratic acid aqueous solution by adding water;

(e.2") adding a quantity of solid L-arginine to the purified α-ketoglutaratic acid aqueous solution, wherein the quantity of the solid L-arginine is equals to one or two equivalent mole of the purified α-ketoglutaratic acid aqueous solution;

(e.3") obtaining a resulting L-arginine α-ketoglutarate 1:1 or 2:1 solution from step (e.2"), wherein a pH of the resulting L-arginine α-ketoglutarate 1:1 solution is approximately 3~4 and a pH of the resulting L-arginine α-ketoglutarate 2:1 solution is approximately 6.5~7; and (e.4") obtaining a final product of L-arginine α-ketoglutarate 1:1 or 2:1 from step (e.3") through spay drying, wherein a yield of the final product is approximately 94% for L-arginine α-ketoglutarate 1:1 or 97% for L-arginine α-ketoglutarate 2:1.

Still further objects and advantages will become apparent from a consideration of the ensuing description and drawings.

These and other objectives, features, and advantages of the present invention will become apparent from the following detailed description, the accompanying drawings, and the appended claims.

DETAILED DESCRIPTION OF THE PREFERRED EMBODIMENT

Figure 1:
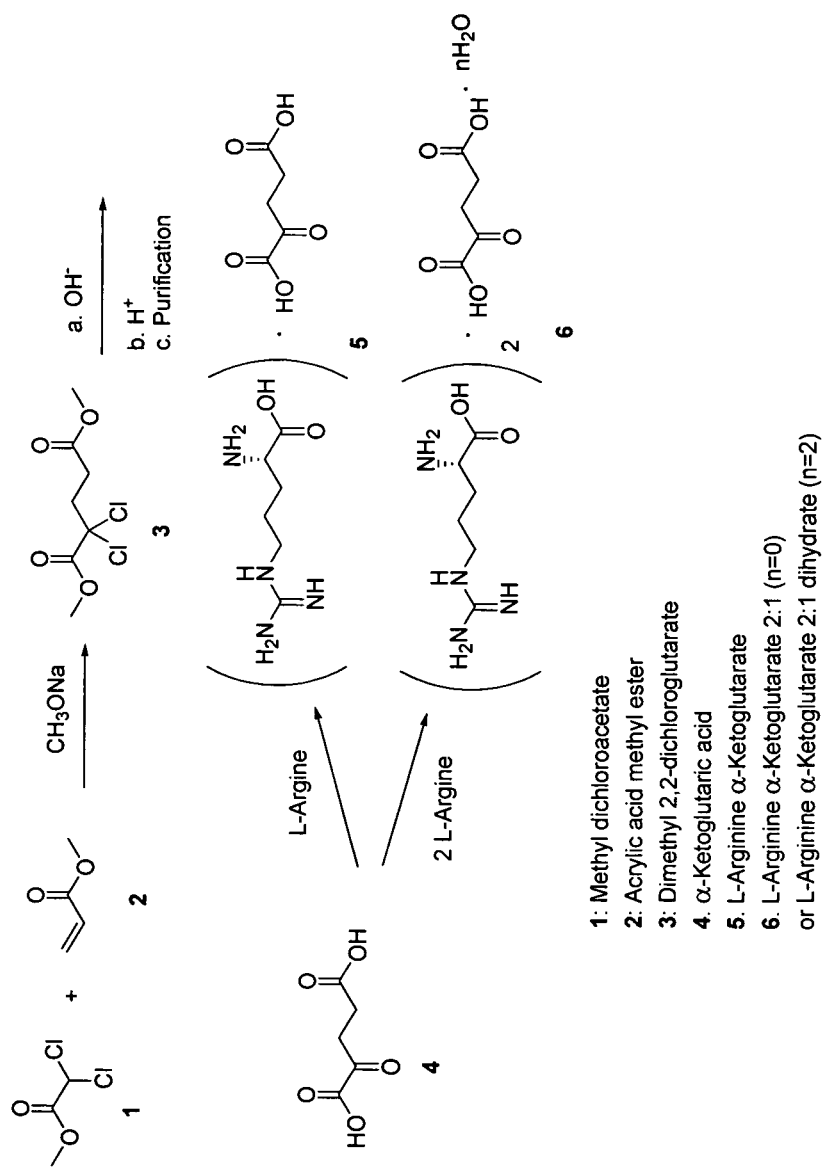
FIG. 1 is a schematic illustration of a process of preparation of α-ketoglutaric acid according to a preferred embodiment of the present invention.
Figure 2:
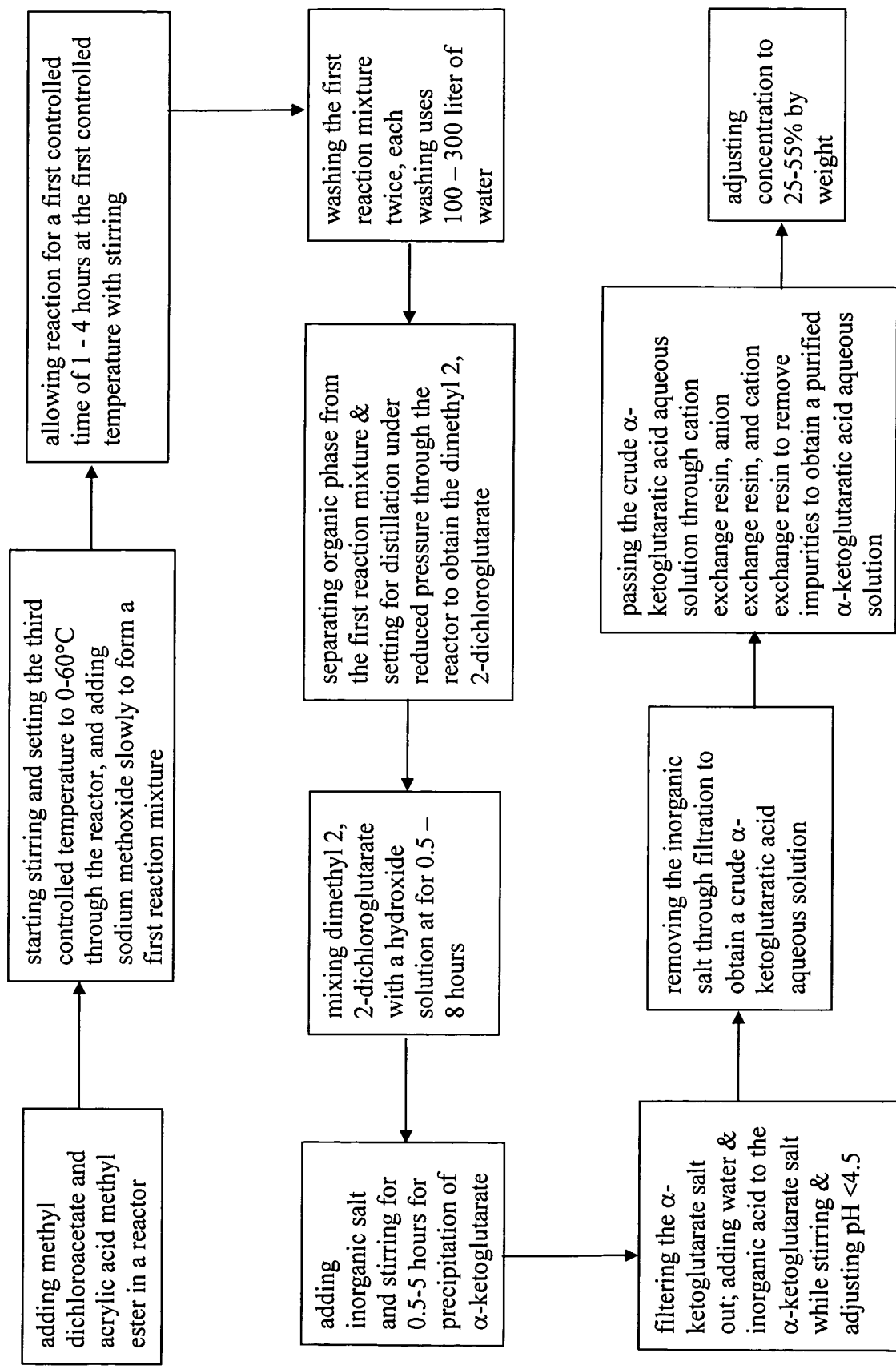
FIG. 2 is a block diagram of a process of preparation of α-ketoglutaric acid according to the above preferred embodiment of the present invention.

Referring to FIGS. 1 and 2 of the drawings, a process of preparation of α-ketoglutaric acid according to a preferred embodiment of the present invention comprises the steps of:

(a) reacting methyl dichloroacetate and acrylic acid methyl ester with sodium methoxide to obtain dimethyl 2,2-dichloroglutarate;

(b) reacting dimethyl 2,2-dichloroglutarate with a hydroxide solution to obtain a crude α-ketoglutaratic acid aqueous solution;

(c) purifying the crude α-ketoglutaratic acid aqueous solution to obtain a purified α-ketoglutaratic acid aqueous solution; and (d) adjusting a concentration of the purified α-ketoglutaratic acid aqueous solution by adding water.

In particular, the preparation of dimethyl 2,2-dichloroglutarate is further described as follows:

In a 3000 liter reactor, methyl dichloroacetate and acrylic acid methyl ester are added. The stirring is controlled to start and a first controlled temperature is adjusted to 0-60° C. Then, sodium methoxide is added slowly to form a first reaction mixture. After the sodium methoxide is added, the first reaction mixture is stirred at the first controlled temperature for 1-4 hours. Subsequently, 100-300 liter of water is added to wash the first reaction mixture. The first reaction mixture is washed with water twice. The organic phase is then separated and distillation under reduced pressure is set to obtain dimethyl 2,2-dichloroglutarate.

In other words, the step (a) is carried out through the following steps:

(a.1) adding methyl dichloroacetate and acrylic acid methyl ester in a reactor;

(a.2) start stirring and setting a first controlled temperature of 0-60° C. through the reactor;

(a.3) adding sodium methoxide slowly to form a first reaction mixture;

(a.4) allowing reaction for 1-4 hours in the reactor at the first controlled temperature with stirring;

(a.5) washing the first reaction mixture after step (i.4) twice, wherein, preferably, 100-300 liter of water is added for each washing; and (a.6) separating organic phase from the first reaction mixture in step (i.5), and setting for distillation under reduced pressure through the reactor to obtain dimethyl 2,2-dichloroglutarate.

It is worth mentioning that no organic solvent is used in the preparation of dimethyl 2,2-dichloroglutarate, as illustrated in the above process.

The preparation of α-ketoglutaratic acid from the dimethyl 2,2-dichloroglutarate obtained from the above steps (a.1) to (a.6) is further described as follows:

Dimethyl 2,2-dichloroglutarate obtained from the above method is mixed with a hydroxide solution at a second controlled temperature for 0.5-8 hours to form a second mixture. Inorganic salt is added to the second mixture and is stirred for 0.5-5 hours to form a large amount precipitate. The second mixture is then filtered to obtain α-ketoglutarate salt, which is stirred with water and inorganic acid to pH≤4.5. The inorganic salt is then removed through filtration to obtain a crude α-ketoglutaratic acid aqueous solution.

In other words, the step (b) is carried out through the following steps:

(b.1) mixing the dimethyl 2,2-dichloroglutarate obtained from step (i) with a hydroxide solution at a second controlled temperature for 0.5-8 hours to form a second mixture;

(b.2) adding inorganic salt to the second mixture and stirring for 0.5-5 hours for precipitation of α-ketoglutarate salt;

(b.3) filtering the α-ketoglutarate salt out; adding water and inorganic acid to the α-ketoglutarate salt while stirring and adjusting a pH to pH≤4.5; and (b.4) removing the inorganic salt through filtration to obtain the crude α-ketoglutaratic acid aqueous solution.

Preferably, the purification of α-ketoglutaratic acid is as follows:

The crude α-ketoglutaratic acid aqueous solution obtained from the above process is passed through cation exchange resin, anion exchange resin, and cation exchange resin to remove impurities. Then, the aqueous solution obtained is concentrated to 25-55% by weight, which is suitable for use as the starting material for preparation of L-arginine α-ketoglutarate 1:1 and 2:1.

In other words, the step (c) is carried out through the following steps:

(c.1) passing the crude α-ketoglutaratic acid aqueous solution through cation exchange resin, anion exchange resin, and cation exchange resin to remove impurities to obtain a purified α-ketoglutaratic acid aqueous solution; and (c.2) adjusting a concentration of the purified α-ketoglutaratic acid aqueous solution to 25-55% by weight.

It is worth mentioning that in step (c.1), both cation and anion exchange resins are used to remove impurities effectively.

The process of preparation of α-ketoglutaric acid according to the preferred embodiment of the present invention has an overall yield of 75%. While avoiding the use of massive organic solvents, the process of the present invention has a remarkable high yield. In other words, a process of preparation of α-ketoglutaric acid is realized for mass production with low manufacturing cost and shortened production time.

Figure 3:
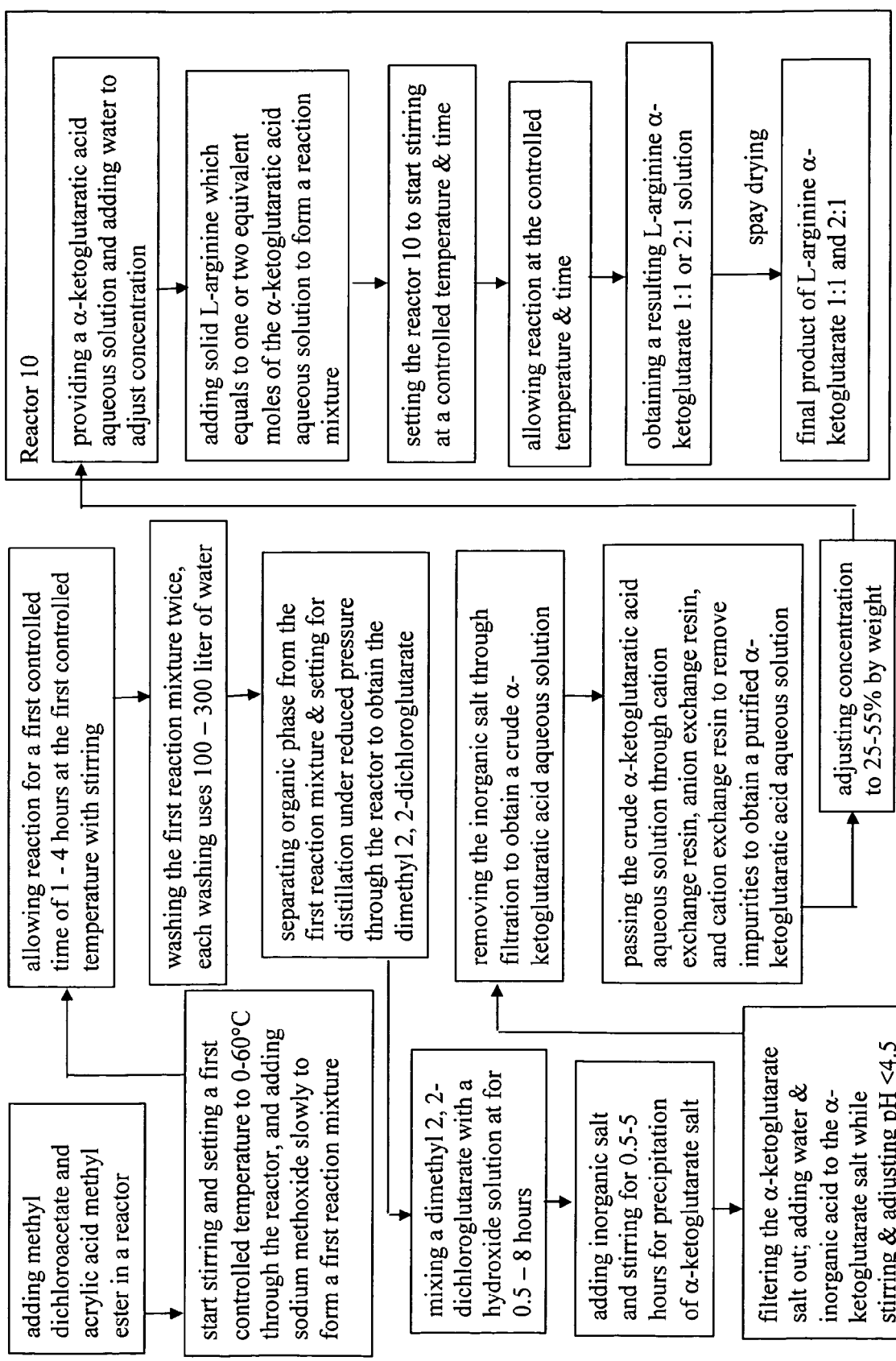
FIG. 3 is a block diagram of a process of preparation of α-ketoglutaric acid method for the mass production of L-arginine α-ketoglutarate 1:1 and 2:1 according to the above preferred embodiment of the present invention.

Referring to FIG. 3 of the drawings, a process of preparation of α-ketoglutaric acid method for the mass production of L-arginine α-ketoglutarate 1:1 and 2:1 is illustrated.

The preparation of L-arginine α-ketoglutarate 1:1 from the α-ketoglutaric acid obtained from the above process is further described as follows:

In a reactor, the purified and concentrated α-ketoglutaratic acid solution is added followed by water to adjust to a certain concentration. One equivalent mole of solid L-arginine is added while the reaction mixture is being stirred. The temperature is controlled to dissolve all solid and form pH 3-4 L-arginine α-ketoglutarate 1:1 solution. The final product is obtained directly via spray drying with a yield of 94%.

In other words, the preparation of L-arginine α-ketoglutarate 1:1 from the α-ketoglutaratic acid solution is carried out through the following steps:

(e.1) setting a concentration of the purified α-ketoglutaratic acid aqueous solution by adding water;

(e.2) adding a quantity of solid L-arginine to the purified α-ketoglutaratic acid aqueous solution, wherein the quantity of the solid L-arginine is equals to one equivalent mole of the purified α-ketoglutaratic acid aqueous solution;

(e.3) obtaining a resulting L-arginine α-ketoglutarate 1:1 solution from step (e.2), wherein a pH of the resulting L-arginine α-ketoglutarate 1:1 solution is approximately 3~4; and (e.4) obtaining a final product of L-arginine α-ketoglutarate 1:1 from step (e.3) through spay drying, wherein a yield of the final product is approximately 94%.

The preparation of L-arginine α-ketoglutarate 2:1 from the α-ketoglutaric acid obtained from the above process is further described as follows:

In a reactor, the purified and concentrated α-ketoglutaratic acid solution is added followed by water to adjust to a certain concentration. Two equivalent mole of solid L-arginine is added while the reaction mixture is being stirred. The temperature is controlled to dissolve all solid and form pH 6.5-7 L-arginine α-ketoglutarate 2:1 solution. The final product is obtained directly via spray drying with a yield of 97%.

In other words, the preparation of L-arginine α-ketoglutarate 2:1 from the α-ketoglutaratic acid solution is carried out through the following steps:

(e.1') setting a concentration of the purified α-ketoglutaratic acid aqueous solution by adding water;

(e.2') adding a quantity of solid L-arginine to the purified α-ketoglutaratic acid aqueous solution, wherein the quantity of the solid L-arginine is equals to two equivalent mole of the purified α-ketoglutaratic acid aqueous solution;

(e.3') obtaining a resulting L-arginine α-ketoglutarate 2:1 solution from step (e.2), wherein a pH of the resulting L-arginine α-ketoglutarate 2:1 solution is approximately 6.5~7; and (e.4') obtaining a final product of L-arginine α-ketoglutarate 2:1 from step (e.3) through spay drying, wherein a yield of the final product is approximately 97%.

It is worth mentioning that solid L-arginine is added directly to the α-ketoglutaratic acid solution to eliminate the need to prepare L-arginine solution. The product solution is spray dried directly to obtain the final product in dry product powder. Compared to the conventional processes, the method of preparation of the present invention eliminates the use of a large amount of organic solvents and reduces the production time and cost, which are the keys to success for mass production.

One skilled in the art will understand that the embodiment of the present invention as shown in the drawings and described above is exemplary only and not intended to be limiting.

It will thus be seen that the objects of the present invention have been fully and effectively accomplished. It embodiments have been shown and described for the purposes of illustrating the functional and structural principles of the present invention and is subject to change without departure from such principles. Therefore, this invention includes all modifications encompassed within the spirit and scope of the following claims.

What is claimed is:

1. A process of preparation of α-ketoglutaric acid for mass production of L-arginine α-ketoglutarate 1:1 and 2:1 comprising the steps of:

(a) reacting methyl dichloroacetate and acrylic acid methyl ester with sodium methoxide to obtain Dimethyl 2,2-dichloroglutarate;

(b) reacting the dimethyl 2,2-dichloroglutarate from step (a) with hydroxide solution to obtain crude α-ketoglutaric acid aqueous solution;

(c) purifying the crude α-ketoglutaric acid aqueous solution to obtain purified α-ketoglutaric acid aqueous solution;

(d) adjusting the concentration of the purified α-ketoglutaric acid aqueous solution by adding water;

(e.1') setting the concentration of the purified α-ketoglutaric acid aqueous solution by adding water;

(e.2') adding a quantity of solid L-arginine to the purified α-ketoglutaric acid aqueous solution, wherein the quantity of the solid L-arginine is equal to two equivalent mole of the purified α-ketoglutaric acid aqueous solution;

(e.3') obtaining a resulting L-arginine α-ketoglutarate 2:1 solution from step (e.2), wherein the pH of the resulting L-arginine α-ketoglutarate 2:1 solution is approximately 6.5~7; and (e.4') obtaining a final product of L-arginine α-ketoglutarate 2:1 from step (e.3) through spray drying, wherein the yield of the final product is approximately 97%.

2. A process of preparation of α-ketoglutaric acid for mass production of L-arginine α-ketoglutarate 1:1 and 2:1 comprising the steps of:

(a) reacting methyl dichloroacetate and acrylic acid methyl ester with sodium methoxide to obtain Dimethyl 2,2-dichloroglutarate, wherein the step (a) comprises the steps of:

(a.1) adding methyl dichloroacetate and acrylic acid methyl ester in a reactor;

(a.2) starting stirring and setting a first controlled temperature of 0-60° C. through the reactor;

(a.3) adding sodium methoxide slowly to form a first reaction mixture;

(a.4) allowing reaction for 1 to 4 hours in the reactor at the first controlled temperature with stirring;

(a.5) washing the first reaction mixture with water twice, wherein 100 to 300 liter of water is used for each of the washing; and (a.6) separating and removing the organic phase of the first reaction mixture in the step (a.5) and setting the reactor for distillation under reduced pressure to obtain dimethyl 2, 2-dichloroglutarate;

(b) reacting the dimethyl 2,2-dichloroglutarate from step (a) with hydroxide solution to obtain crude α-ketoglutaric acid aqueous solution, wherein the step (b) further comprises the steps of:

(b.1) mixing the dimethyl 2, 2-dichloroglutarate obtained from step (a) with hydroxide solution at a second controlled temperature for 0.5 to 8 hours to form a second mixture;

(b.2) adding inorganic salt to the second mixture and stirring for 0.5 to 5 hours for precipitation of α-ketoglutarate salt;

(b.3) filtering the α-ketoglutarate salt out, adding water and inorganic acid to the α-ketoglutarate salt while stirring and adjusting the pH to pH≤4.5; and (b.4) removing the inorganic salt through filtration to obtain the crude α-ketoglutaric acid aqueous solution;

(c) purifying the crude α-ketoglutaric acid aqueous solution to obtain purified α-ketoglutaric acid aqueous solution, wherein the step (c) further comprises a step of:

(c.1) passing the crude α-ketoglutaric acid aqueous solution through cation exchange resin, anion exchange resin, and cation exchange resin in series to remove impurities to obtain a purified α-ketoglutaric acid aqueous solution; and (c.2) adjusting the concentration of the purified α-ketoglutaric acid aqueous solution to 25-55% by weight;

(d) adjusting the concentration of the purified α-ketoglutaric acid aqueous solution by adding water;

(e.1') setting the concentration of the purified α-ketoglutaric acid aqueous solution by adding water;

(e.2') adding a quantity of solid L-arginine to the purified α-ketoglutaric acid aqueous solution, wherein the quantity of the solid L-arginine is equal to two equivalent mole of the purified α-ketoglutaric acid aqueous solution;

(e.3') obtaining a resulting L-arginine α-ketoglutarate 2:1 solution from step (e.2), wherein the pH of the resulting L-arginine α-ketoglutarate 2:1 solution is approximately 6.5~7; and (e.4') obtaining a final product of L-arginine α-ketoglutarate 2:1 from step (e.3) through spray drying, wherein the yield of the final product is approximately 97%.

* * * * *